United States Patent [19]

Likhite

[11] 4,285,930

[45] Aug. 25, 1981

[54] ANTIGENS COMPRISING IMMUNOSTIMULANT ADJUVANTS AND THEIR USE IN IMMUNOTHERAPY

[76] Inventor: Vilas V. Likhite, 317 Marlborough St., Boston, Mass. 02116

[21] Appl. No.: 93,171

[22] Filed: Nov. 13, 1979

Related U.S. Application Data

[63] Continuation of Ser. No. 858,847, Dec. 8, 1977, abandoned.

[51] Int. Cl.³ ..................... A61K 39/10; A61K 39/00
[52] U.S. Cl. ......................................... 424/92; 424/88
[58] Field of Search ...................... 424/88, 92; 424/85, 424/87

[56] References Cited

PUBLICATIONS

Likhite, V. V., "Clinical Cancer Immunotherapy: Experience in Breast and Lung Cancer", Immunocancerology in Solid Tumors, (Martin, M. and Dionne, L., eds.), pp. 135–141, 1976.

Likhite, V. V., IRCS Medical Science, 4,565, (1976).

*Primary Examiner*—Delbert R. Phillips
*Assistant Examiner*—Blondel Hazel
*Attorney, Agent, or Firm*—Richard P. Crowley

[57] ABSTRACT

Antigens are provided which induce relatively large titers of antibodies. These antigens, which may comprise certain strains of microorganisms or a plant extract, can be conjugated to a second antigen by means of an organic coupling agent. The primary antigens of the invention, when chemically coupled to a secondary antigen function as immunostimulant adjuvants. When tumor cells are the secondary antigens, a means for immunotherapeutic treatment of cancer is provided.

6 Claims, No Drawings

ANTIGENS COMPRISING IMMUNOSTIMULANT ADJUVANTS AND THEIR USE IN IMMUNOTHERAPY

This is a continuation of application Ser. No. 858,847, filed Dec. 8, 1977 now abandoned.

BACKGROUND OF THE INVENTION

1. Field of the Invention

This invention relates to certain antigens and antigen conjugates, and to their method of manufacture, useful, in particular, in the production of high titers of antibodies, to the production of these antibodies, and to the use of these conjugated antigens in the immunotherapeutic treatment of cancer.

2. Description of the Prior Art

Immunity is an everyday word applied to a special category of defenses possessed by the body by means of which infectious agents may be checked or destroyed even after they have entered the body tissues. When a person or animal becomes immune to a disease, the immunity is largely due to the development within the body of substances capable of destroying or inactivating the causative agent of the disease, should it gain access to the body at a later time. These substances, known as antibodies or immune bodies, are produced by the body in response to a specific stimulus. Microbes and their products within the body may stimulate the body cells to antibody production. Other substances that may accomplish the same effect include red blood cells and serum from other animals, and other proteins. These substances are collectively known as antigens and are generally of high molecular weight substances of a protein nature, but in some cases complex carbohydrates (polysaccharides) may act as antigens.

Antigens are substances that stimulate the formation of antibodies within an animal and react observably with that antibody. They generally possess a high molecular weight of 10,000 or more. While the list below is not meant to be all inclusive (a detailed description is set forth in P. L. Carpenter, *Immunology and Serology*, 2nd Edition, 1968), typical antigens may be classified as follows:

(1) protein antigens, such as ceruloplasmin and serum albumin;
(2) bacterial antigens, such as teickoic acids, flagellar antigens, capsular polysaccharides, and extra-cellular bacterial products and toxins;
(3) blood group antigens, such as glycoproteins and glycolipids;
(4) viruses, such as animal, plant, and bacterial viruses;
(5) conjugated and synthetic antigens, such as protein-hapten conjugates, and synthetic polypeptides; and
(6) nucleic acids, such as ribonucleic acid and deoxyribonucleic acid.

Immunity may be natural or acquired, and in the latter case may be acquired naturally or artificially. Artificial immunity, as is well known, can be either passive, i.e., by injection of an antiserum (prophylactic, therapeutic), or active, as by vaccination with, for example, live or dead organisms.

Immunization procedures are important in the prevention of various diseases including viral diseases. There is also considerable evidence that viruses do cause various kinds of tumors and cancerous growths, particularly in lower animals such as rabbits, mice, chickens, and hamsters. Various investigators, including the present applicant, have also been active in their attempt to discover agents that might be effective in cancer immunotherapy. See Lekhite, V. V., "Clinical Cancer Immunotherapy: Experience in Breast and Lung Cancer," in *Immunocancerology in Solid Tumors*, (Martin, M. and Dionne, L., eds.) pp. 135–141. (Stratton, 1976). "Rejection of Tumor Metastases in Fisher 344 Rats Following Administration of Killed *Corynebacterium parvum*," *Cancer Immunology and Immunotherapy*, (1977), Vol. 2, pp. 173–178. V. V. Likhite.

In response to an injection of antigens, the body of an animal produces specific antibodies which react with and neutralize the antigens. Antibodies are classified as proteins with the solubility of globulins and the electrophoretic mobility of gamma globulin. The molecular weight of gamma globulins, or as they are also called "immune globulins," varies from 160,000 to 1,000,000 and these immune globulins (Ig) are subgrouped into five classes, according to molecular weight, i.e., Ig G, Ig A, Ig D, Ig E, and Ig M. The Ig G class, or group, is the most prevalent in serum and is characterized by a molecular weight of 160,000. The Ig M class is the least prevalent and is characterized by a molecular weight of 1,000,000.

Sometimes it is necessary that a large supply of antibodies appear in a person's blood immediately in order to combat an overwhelming infection already present in the body. Accordingly, the patient must receive ready-made antibodies, and various means are known for the manufacture and recovery of antigens and antibodies, these being merely exemplified by U.S. Pat. Nos. 3,652,761 and 3,843,444.

In U.S. Pat. No. 3,652,761, there is disclosed an immunochemical composite comprising an antigen or antibody chemically coupled to an inorganic carrier. As the antigen or antibody becomes insolubilized, when so coupled, this, according to the patentee, provides a better means of recovery of a more pure antigen or antibody.

U.S. Pat. No. 3,843,444, which issued to applicant on Oct. 22, 1974, discloses a means for concentration, separation, and recovery of macromolecular substances having mutual attraction for one another, particularly biological substances such as antibodies and antigens. The invention makes use of the discovery that antigens and antibodies, which are specific for one another, can be preferentially attracted to opposite surfaces of thin semipermeable members.

These various known procedures for manufacture and recovery of antigens and antibodies, while satisfactory to a degree, are attendant with certain disadvantages. One major disadvantage with some prior known systems results from the fact that antigens and antibodies are mutually attracted to one another. This attraction interferes with purification and recovery of antibodies. The recovered product, in many instances, has been markedly reduced to a fraction, e.g. 5–20%, of the original physiological activity. When an animal receives repeated injections of a given antigen, the induced specific antibody response in the host animal against the injected antigen represents a relatively small amount, usually less than 1%, of the serum globulin pool. The quantitive response, moreover, has not been improved beyond the host capabilities.

There is a need, not only for a method of producing larger quantities of antibodies within a biological system, but also improved methods of recovery of antibodies without loss of appreciable activity.

SUMMARY OF THE INVENTION

The above disadvantages are overcome by the present invention which comprises in its basic aspects certain antigens and antigen conjugates useful in the production of higher titers of specific antibodies than obtainable heretofor. The antigens of the invention are also found useful in diagnostic medicine, analytical biochemistry, and immunotherapy.

The invention in its more specific aspects is an antigen which comprises certain killed microorganisms or a plant extract which when chemically coupled to another antigen acts as an immunostimulant adjuvant, inducing high titer antibody response specific to the antigen conjugate. This secondary antigen can be a physiological substance such as a virus or tumor cells in which case the antigen conjugate functions as a chemotherapeutic product.

Quite advantageously, although all the antigens of the present invention can be used in the manufacture of high titers of specific antibodies, a different response can be obtained in the host biological system, depending on the particular antigen used. When the primary antigen is a new strain of *Listeria monocytogenes* the invention provides, most importantly, a means by which specific high molecular weight antibodies, i.e. Ig M, specific to the antigen can be produced, when the antigen is injected into an animal. These antibodies are recoverable by rather simple procedures that allow for easy separation due to the inherent characteristics of these high molecular weight antibodies, and most importantly without impairing their physiological properties to any great degree, if at all.

The specific Ig M antibodies of the invention, Ig M antibodies being pentamers of Ig G antibodies, can be separated, moreover, into Ig G antibodies by means of physiologically mild reducing agents without appreciable loss of their specific activity.

The specific Ig M antibodies of the invention can be, moreover, quite advantageously, tagged or labeled with a vital dye (stain) for use in diagnostic applications. This permits use of a conventional light microscopy instead of fluroscent microscopy.

Ig M antibodies according to the invention can, moreover, be coupled with chemotherapeutic agents such as antibodies and anticancer drugs for the treatment of the specific disease-causing agents (towards which the antibody has already been formed). Bacteria, viruses, tumor cells and other infectious agents can be combined with the immunopotentiating agent and such combination used a therapuetic substance.

The new strain of *Corynebacteriam parvum* and *Corynebacteriam paragranulosum* according to the invention not only induces high titers of Ig G, but also advantageously affect the macrophage systems.

The third microorganism antigen of the invention, a new strain of *Bordetella pertussis,* as well as the plant extract (Species *Rhus*) induces high titers of Ig E.

Subcultures of the newly discovered bacteria strains *Bordetella pertussis akka, Listeria monocytogenes akka, Corynebacteriam parvum akka,* and *Corynebacteriam paragranulosum,* used in the practice of the invention have been deposited with, and can be obtained upon request from the permanent collection of, the Northern Regional Research Laboratories, Agricultural Research Services, U.S. Department of Agriculture, Peoria, IL, U.S.A. Their accession numbers in this repository of NRRL B-11,232; NRRL B-11,233; NRRL B-11,234; NRRL B-11,235; respectively.

DETAILED DESCRIPTION OF THE INVENTION AND THE PREFERRED EMBODIMENTS THEREOF

In accordance with one aspect of the invention, certain antigens have been discovered which, when injected into an animal, result in a response to evoke relatively high titers of antibody.

Those antigens which have been found to accomplish this desirable antibody response, are novel killed strains of three bacteria, *Listeria monocytogenes akka, Bordetella pertussis akka,* and *Corynebacteriam parvum akka* and *Corynebacteriam paragranulosum,* and a plant extract from the plant species *Rhus.*

Other antigens, i.e. secondary antigens, can be sensitized to evoke the same high antibody response by chemically coupling them to the above-mentioned primary antigens. In this regard the primary antigens function as an innumopotentiating agent, or as such might also be called, an immupostimulant adjuvant.

The secondary antigens can be any of those commonly known as antigens, however, the secondary antigen of the invention can, quite advantageously, be a physiological substance such viruses, hormones, bacteria, and tumor cells. This results from the fact that a common characteristic of the primary antigens is their ability to function as immunotherapeutic agents. Thus, when a secondary antigen such as a live tumor cell is coupled to a primary antigen such as the novel strain of *Bordetella pertussis akka,* a chemotherapeutic product results which, when injected into an animal having that tumor induces a response that results in rejection of the tumor. Similarly when an antigen conjugate couples a virus with an immunopotentiating agent in accordance with the invention, the injection of such a conjugate into an animal affects treatment of the viral infection by stimulation of host defenses against viral infections.

Coupling of the secondary antigen to the primary antigen can be accomplished by means of various chemical agents providing two reactive sites such as, for example, bisdiazobenzidine, glutaraldehyde, m-xylenediisocyanate, di-iodoacetate, and a diisocyanate such as toluene-2,4 diisocyanate. The latter coupling agent is more preferred for a number of reasons. First of all the NCO groups readily react with free $NH_2$ groups. However, and this is a most desirable feature in using toluene-2,4 diisocyanate, only the NCO group at the 4th carbon remains active at 4° C. Thus, its use as a coupling agent permits coupling of the killed bacteria strain or plant extract first at the 4th carbon position, followed by coupling of a second antigen at the second carbon position. If desired, however, the so-called "secondary antigen" can be coupled to the 4th carbon position first, followed by coupling of the immunostimulant adjuvant, or primary antigen, to the 2nd carbon position.

Although a common characteristic of the microorganism antigens of the present invention is their ability to act as therapeutic agents, each of the primary antigens differ somewhat in the antibody response induced. Nevertheless, a high titer is common, sometimes reaching quantities as high as 6 gm percent in the host serum, an unexpectedly high result.

The invention provides in the use of the novel strain of *Listeria monocytogenes* not only a means of producing large quantities of high molecular weight antibodies, Ig M, but also a means for the recovery of these antibodies as pure and active antigen—specific antibodies. This results from the fact that such antibodies are characterized by insolubility in cold temperature, e.g. 4° C., making for ease in separation and recovery of a purified product, from the serum, as hereinafter more fully disclosed. The Ig M goes back into solution when suspended in physiological buffer solution with heating to 31° C.

As the Ig M antibodies maintain their antigen specific immunochemical characteristics, they are more desirable for use in diagnostic and therapeutic immunology. The purified antibody, i.e., the antibody recovered, reacts only with the *Listeria monocytogenes* organism or the coupled antigen and organism, according to the invention.

The Ig M antibodies can, if desired, be separated into five subunits of Ig G antibodies, which also exhibit the specificities as the Ig M antibodies, by exposure to various mild physiological reducing agents. Examples of these are mercaptoethanol and cysteine. Thus, it is possible to produce higher titers than heretofore of Ig G antibodies, and of a desirable purity, which can be used in various immunochemical applications including radioimmunoassay.

Although recovery of Ig M antibodies can be based on their insolubility at cold temperatures, this method of recovery need not be the only one employed. Sheep red blood cells can be used, according to conventional techniques. Other methods of recovery of Ig M include column chromatography using sephadex or sepharose 6200, the Ig M being represented in the first peak of protein eluted. These alternative methods are less preferred, however, as they do result in some, though not appreciable, loss of specific activity.

It has also been discovered, quite unexpectedly, that a protein extract from the culture medium in which the microorganisms of the invention are grown induces the same responses as the microorganism.

After the microorganism strain is recovered, the medium is saturated with $(NH_4)_2SO_4$, and allowed to precipitate out overnight. It is then dialized against standard buffer and used as primary antigen.

The invention also comprises a method for the treatment of growing tumors comprising injecting the animal having the tumor repeatedly with an antigen comprising a like living tumor cell coupled to an immunostimulant adjuvant characterized by its ability to activate the reticuloendothelial and lympho-proliferative systems toward sensitizing antigens.

The invention may be more fully understood by reference to the following examples which illustrate certain embodiments of the invention.

ISOLATION OF MICROORGANISMS

EXAMPLE 1

Using conventional sterile technique a novel strain of *Listeria monocytogenes* was isolated from a patient having lung cancer but who died from listeriosis. The isolate was grown in 500 ml standard culture medium (Todd-Hewitt), according to known procedures, over a period of about 24 hours.

The culture medium was then heated at 60° C. for a sufficient time, e.g. about one hour, to kill the bacteria. This was determined by a lack of growth when the material was placed on blood agar plates.

The broth was next centrifuged according to conventional techniques at 3000 g for 20 minutes to harvest the killed bacteria cells, the supernate being saved for extraction of the associated active protein.

The recovered killed bacteria cells were then suspended in 50 ml standard Phosphate Buffered Saline (PBS, pH 7.4) and this suspension then centrifuged, as previously described, and the bacteria cells again harvested. The procedure was then twice repeated to make certain the cells were clean.

EXAMPLE 2

Using the procedure as described in Example 1, a novel strain of the bacteria *Bordetella pertussis* was isolated and recovered from a child patient having hooping cough.

EXAMPLE 3

The procedure of Example 1 was used to recover the novel strain, *Corynebacteriam parvum akka,* from a patient having a malignant colonic cancer (w/o metastases) and a huge spleen, but who died of a heart attack. The medium used, however, was a standard anerobic/-heart brain infusion broth. Similarly, the microorganism *Corynebacteriam paragranulosum* was isolated.

PRODUCTION OF PLANT EXTRACT

EXAMPLE 4

Cut leaves from the plant *Rhus* were homogenized with 95% ethanol, after which the supernate was centrifuged off. The residue was allowed to dry, after which it was ready for use.

PRODUCTION OF ANTIBODY USING PRIMARY ANTIGENS

EXAMPLE 5

The bacteria strains of Examples 1-3 and the plant extract of Example 4 were each suspended in standard PBS, p. 7.4, according to usual technique and separately injected into experimental animals over a period of several weeks.

When the animals were bled and antibody titer determined, it was found to be unexpectedly high. The antibodies recovered were antigen-specific, depending upon the particular antigen utilized. Ig M was produced using the strain *Listeria monocytogenes akka;* the strain *Corynbacteriam parvum akka,* as did *Corynebacteriam paragranulosum,* resulted in Ig G; and the strains of *B. pertussis akka* and the plant extract induced Ig E antibodies.

PRODUCTION OF ANTIGEN CONJUGATE

EXAMPLE 6

The harvested killed bacteria cells of Example 1 (*Listeria monocytogenes*) were resuspended in 6 ml standard PBS, pH 8.6, in a 25 ml Ehrlenmeyer flask, and the contents placed at 4° C. for 30 minutes. Toluene-2,4 diisocyanate (TDIC), which meanwhile had been cooled to 4° C., was then added dropwise to the flask, with constant stirring, over a period of 1 hour, 100 mg total being added. This solution was then allowed to sit for 30 minutes in order that the TDIC was conjugated with the killed bacteria.

The suspension was then centrifuged (3000 g for 20 minutes) and the supernatant material discarded. The recovered antigen conjugate (bacteria - TDIC) was then resuspended in 8 ml std. PBS, pH 7.4, and again washed by centrifugation, as before.

The washed antigen conjugate was then resuspended in 6 ml std. PBS, pH 7.4, and 500 mg bovine serum albumin (50% solution in std. PBS, pH 7.4, dialyzed previously according to conventional techniques) was then added to the suspension. This mixture was then placed at 37° C. and stirred (magnetic stirrer) for 1 hour, after which it was allowed to sit for 30 minutes. The suspension was then washed by centrifugation, as before described. It was then determined according to usual techniques that 2 mg albumin were conjugated to $10^9$ bacterial cells. These solutions were then stored at $-70°$ C. until ready for use.

EXAMPLE 7

In a manner as disclosed in Example 6, the strain of *B. pertussis* disclosed in Example 2 is coupled to toluene-2,4 diisocyanate, except that rather than reducing the temperature so as to couple the bacteria to the carbon 4-NCO group, it was coupled to the carbon 2-NCO group, at 37° C. Live tumor cells (T 1699 - mammary adenocarcinoma, The Jackson Laboratory, Bal Harbour, Maine, U.S.A.) were first coupled at the 4th carbon site.

PRODUCTION OF ANTIGEN-ANTIBODY COMPLEX

EXAMPLE 8

0.25 ml of the solution of Example 6 were injected intravenously into each of several experimental rabbits at weekly intervals for five weeks, during which time the rabbits were producing antibodies in response to the presented antigen conjugate.

A week following the last injection, the rabbits were bled (from 50 ml to 120 ml of blood was obtained from each rabbit). The antibody titer was determined according to conventional procedures and was found to be unexpectedly high. Measurements were discontinued after 1/6,000,000 dilution of the serum.

At this point, the blood can either be allowed to heparinize or clot (at 37° C.) for further processing.

RECOVERY OF ANTIBODY

EXAMPLE 9

The blood samples from the rabbits of Example 8 were allowed to clot and the serum then placed at 4° C. for 24 hours. At this temperature the gamma M globulins (due to their inherent nature) precipitate and can then be recovered. This was accomplished by centrifugation (1000 g×10 min.) at 4° C., after which the precipitated gamma M globulins were washed twice by centrifugation, using cold std. PBS, pH 7.4.

The recovered precipitate was then resuspended in std. PBS, pH 7.4, depending on the original volume of blood, and these suspensions warmed to room temperature, at which time the precipitate became soluble.

In this manner from 2 to 7 grams of gamma M globulins were separated. 6 mg of the globulins recovered reflected about 1/250,000 titer to albumin, indicating that all antibody recovered was albumin specific.

SEPARATION GAMMA M GLOBULINS INTO SUBUNITS

EXAMPLE 10

An equal volume of the Ig M from Example 9 was added to 0.06 M cysteine in std. PBS, pH 7.4 and this mixture was incubated at 37° C. for two hours. This caused the gamma M globulins to separate into gamma G globulin subunits. These are found to react in the same manner with the albumin, without loss of specific activity.

USE OF ANTIGEN CONJUGATE AS CHEMOTHERAPEUTIC PRODUCT

EXAMPLE 11

This example is directed to the immunotherapeutic treatment of growing tumors by the injection of mice with the *Bordetella pertussis* (new strain) - ICTD - tumor cell antigen conjugate of Example 7, the data having been published in IRCS Medical Science, 4,565 (1976), this article being authored by applicant and incorporated completely herein by reference.

Approximately $10^6$ living syngeneic T1699 mammary adenocarcinoma cells (The Jackson Laboratory) were transplanted subcutaneously in the lateral posterial flank of 100 previously unsensitized DBA/2 mice (females, age 5 weeks, The Jackson Laboratory). Seven days later (mean tumor diameter 0.2 cm) the mice were separated into 5 goups of 20 animals each.

The mice in each group were then each given weekly (×4) intraperitoneal injections of one of the following: (1) Standard Phosphate Buffered Saline, pH 7.4; (2) living $10^6$ T1699 cells coupled with ICTD at carbon position 4; (3) new strain killed *Bordetella pertussis* ($5\times10^7$ organisms) according to invention; (4) separately new strain killed *Bordetella pertussis* ($5\times10^7$) and living $10^6$ T1699 tumor cells; and (5) live $10^6$ T1699 tumor cells coupled specifically with $5\times10^7$ new strain killed *Bordetella pertussis* using ICTD (ICTD, as disclosed in Example 7 allows for first coupling the tumor cells only at carbon position 4 at 4° C., and then *B. pertussis* at carbon position 2 which is active at 37° C.; however, reverse could be done also, if desired). The mice were inspected at twice weekly intervals and two tumor diameters were measured on each mouse until death.

Only the mice of group 5, i.e., the mice treated with the chemotherapeutic product comprising tumor cell - ICTD - *B. pertussis* conjugate, according to the invention, survived. These animals exhibited expected rates of tumor growth for 8 days, even after therapy was initiated; however, this was followed by regression of tumor size and disappearance of the tumor in 20/20 mice. These particular mice have survived tumor free for more than 18 months.

The mice in the remaining four groups all died with growing tumors and metastases (seen on autopsy). Of these, the mice in groups 3 and 4, i.e., those treated with killed *B. pertussis* (new strain) alone, or together with separate injections of T1699 tumor cells, surprisingly exhibited accelerated rates of tumor growth.

These studies were repeated and similar results were obtained.

EXAMPLE 12

The immunotherapy of Example 11 was repeated except that $SAD_2$ sarcoma and $CAD_2$ mammary adenocarcinoma syngeneic to DBA/2 mice and the R3230 and 13762 mammary adenocarcinomas syngeneic to Fischer 344 rats were evaluated, rather than the T1699 tumor cells.

Similar results were obtained and long term tumor free survivals.

As many different embodiments of this invention will now have occurred to those skilled in the art, it is to be understood that the specific embodiments of the invention as presented herein are intended by way of illustration only and are not limiting on the invention, but that the limitations thereon can be determined only from the appended claims.

What I claim is:

1. An antigen conjugate useful in the production of relatively large titers of antibodies specific thereto, which antigen conjugate comprises an immunostimulant adjuvant consisting essentially of a primary antigen of a killed strain of *B. pertussis* mutant strain NRRL B-11,232 coupled by a diisocyanate-coupling agent to a secondary antigen comprising living adenocarcinoma tumor cells.

2. The antigen conjugate of claim 1 wherein the coupling agent is toluene-2,4-diisocyanate, with the primary antigen coupled at one reactive NCO site of the diisocyanate-coupling agent, and the secondary antigen of the living tumor cells coupled at the other reactive NCO site of the diisocyanate-coupling agent.

3. The antigen conjugate of claim 1 wherein the living tumor cell comprises T-1699 mammary adenocarcinoma cells.

4. An antigen conjugate useful in the production of relatively large titers of antibodies specific thereto which antigen conjugate consists essentially of a primary antigen of a killed mutant strain of *B. pertussis* NRRL B-11,232 coupled with toluene-2,4 diisocyanate to a secondary antigen comprising living T-1699 mammary adenocarcinoma tumor cells with the primary antigen coupled at one reactive NCO site position and the secondary antigen coupled at the other reactive NCO site position of the coupling agent.

5. The antigen conjugate of claim 1 wherein the diisocyanate coupling agent comprises toluene-2,4-diisocyanate or m-xylenediisocyanate.

6. The antigen conjugate of claim 1 wherein the diisocyanate coupling agent is toluene-2,4-diisocyanate and the killed strain of *B. pertussis* mutant strain is first coupled to the 4-carbon position of the diisocyanate.

* * * * *